United States Patent
Steidl

(10) Patent No.: US 8,097,077 B2
(45) Date of Patent: Jan. 17, 2012

(54) STRENGHTENED, PRESSABLE CERAMIC COMPOSITIONS FOR DENTAL PURPOSES

(75) Inventor: Jurgen Steidl, Wollstadt (DE)

(73) Assignee: Heraeus Kulzer GmbH, Hanau (DE)

( * ) Notice: Subject to any disclaimer, the term of this patent is extended or adjusted under 35 U.S.C. 154(b) by 449 days.

(21) Appl. No.: 12/399,234

(22) Filed: Mar. 6, 2009

(65) Prior Publication Data
US 2009/0221413 A1 Sep. 3, 2009

Related U.S. Application Data

(63) Continuation-in-part of application No. 11/052,396, filed on Feb. 7, 2005, now abandoned.

(30) Foreign Application Priority Data

Feb. 27, 2004 (DE) .......................... 10 2004 010 138

(51) Int. Cl.
A61K 6/02 (2006.01)
(52) U.S. Cl. ................. 106/35; 501/32; 501/2; 501/59; 501/67; 501/70; 501/73
(58) Field of Classification Search ................. 501/32, 501/2, 59, 67, 70, 73; 106/35
See application file for complete search history.

(56) References Cited

U.S. PATENT DOCUMENTS

| | | | |
|---|---|---|---|
| 4,189,325 A | 2/1980 | Barrett et al. | |
| 4,515,634 A | 5/1985 | Wu et al. | |
| 5,432,130 A | 7/1995 | Rheinberger et al. | |
| 5,713,994 A * | 2/1998 | Kramer et al. | 106/35 |
| 5,916,498 A | 6/1999 | Hofmann et al. | |
| 5,968,856 A | 10/1999 | Schweiger et al. | |
| 6,022,819 A | 2/2000 | Panzera et al. | |
| 6,121,175 A | 9/2000 | Drescher et al. | |
| 6,342,302 B1 | 1/2002 | Steidl et al. | |
| 6,428,614 B1 | 8/2002 | Brodkin et al. | |
| 6,455,451 B1 | 9/2002 | Brodkin et al. | |
| 6,627,569 B1 | 9/2003 | Naumann et al. | |
| 6,761,760 B2 | 7/2004 | Brodkin et al. | |
| 2002/0010063 A1 | 1/2002 | Schweiger et al. | |

FOREIGN PATENT DOCUMENTS

| | | |
|---|---|---|
| DE | 1972552 | 12/1998 |
| DE | 19750794 | 6/1999 |
| DE | 19852516 | 5/2000 |
| DE | 19906240 | 8/2000 |
| EP | 0231773 | 8/1987 |
| EP | 0631995 | 1/1995 |
| WO | 9730678 | 8/1997 |
| WO | 0034196 | 6/2000 |

OTHER PUBLICATIONS

Hoffmann-Axthelm, Lexicon der Zahnmedizin, 1983.
Manfred Kern, Arbeitsgemeinschaft Keramik Prof. Dr. Lothar Probster (Weisbaden-Tubingen); www.ag-keramik.de. new11whoiswho.htm.

* cited by examiner

*Primary Examiner* — Carol M Koslow
(74) *Attorney, Agent, or Firm* — Norris McLaughlin & Marcus PA

(57) ABSTRACT

Pressable glass-ceramic compositions for dental purposes of the composition I, II or III

| | I | | II | | III |
|---|---|---|---|---|---|
| | (percent by weight) | | (percent by weight) | | (percent by weight) |
| $ZrO_2$ | 17-70% | $ZrO_2/Al_2O_3$ | 15-70% | $Al_2O_3$ | 15-70% |
| $SiO_2$ | 17-59% | $SiO_2$ | 17-59% | $SiO_2$ | 17-59% |
| $Al_2O_3$ | 2-15% | $ZrO_2$ | 2-15% | $ZrO_2$ | 2-15% |
| $Y_2O_3$ | 0-6% | $Y_2O_3$ | 0-6% | $Y_2O_3$ | 0-6% |
| $K_2O$ | 3-12.5% | $K_2O$ | 3-12.5% | $K_2O$ | 3-12.5% |
| $Na_2O$ | 0.2-8.5% | $Na_2O$ | 0.2-8.5% | $Na_2O$ | 0.2-8.5% |
| $Li_2O$ | 0-1.5% | $Li_2O$ | 0-1.5% | $Li_2O$ | 0-1.5% |
| CaO | 0.3-2% | CaO | 0.3-2% | CaO | 0.3-2% |
| $B_2O_3$ | 0.1-5% | $B_2O_3$ | 0.1-5% | $B_2O_3$ | 0.1-5% |
| F | 0-2.5% | F | 0-2.5% | F | 0-2.5% |
| $CeO_2$ | 0.2-2% | $CeO_2$ | 0.2-2% | $CeO_2$ | 0.2-2% |
| $TiO_2$ | 0-1.5% | $TiO_2$ | 0-1.5% | $TiO_2$ | 0-1.5% | are particularly suitable for the manufacturing of ceramic veneer frames.

5 Claims, No Drawings

STRENGHTENED, PRESSABLE CERAMIC COMPOSITIONS FOR DENTAL PURPOSES

This application is a Continuation-In-Part of application Ser. No. 11/052,396 filed Feb. 7, 2005, now abandoned.

The invention concerns pressable glass-ceramic compounds for dental purposes that are enhanced with regard to their breaking strength and fracture toughness.

BACKGROUND OF THE INVENTION

A prevalent process for the manufacturing of all-ceramic dental restorations in particular is the so-called press ceramics, in which dental ceramic material is converted to a viscous state under the impact of pressure and heat and is pressed in a form that corresponds to the dental prosthesis. The technique and a press ceramic furnace suitable for this technique are described for example in EP 0 231 773 A1 and has become known as Empress® process (Ivoclar, Schaan, Co., LI). The process is suitable for the manufacturing of (partial) crowns, inlays, onlays, veneers or bridges, and also for the manufacturing of frames for the so-called veneer ceramics technique. In this technique, metal frames are as a rule veneered with ceramics such that a tooth-colored dental prosthesis is finally formed. Correspondingly, all-ceramic frames are formed by means of the press ceramics. The advantage of these all-ceramic frames is that no dark metal can shine through from below the veneer.

The prevalent press ceramic materials attain breaking strengths of 220 MPa [Manfred Kern, Arbeitsgemeinschaft Keramik Prof. Dr. Lothar Pröbster (Wiesbaden-Tübingen) http://www.ag-keramik.de.news11whoiswho.htm]. The materials of the second generation (Empress® 2) are lithium disilicate glass ceramics and attain higher breaking strengths of 350-400 MPa (DE0019750794A1, DE0019647739C2, EP1149058A2). This is explained by the fact that the structure of the lithium disilicate crystals corresponds to the "Mikado" principle. Thus microcracks are prevented. A crack has to either overcome many boundary layers or extend around the crystals so that the crack energy is dissipated.

In dental ceramics, the term breaking strength or breaking boundary means the boundary in pressure load, tensile loading, bending load or torsion load up to which a material can be loaded without breaking. The collapse load is the force that is exerted up to the point of breakage. (Hoffmann-Axthelm, *Lexikon der Zahnmedizin* [Lexicon of Dentistry], 1983).

The bending strength of Empress® press ceramics equals 110 to 120 MPa (Volker Kluthe, Dissertation, http://darwin-.inf.fu-berlin.de/2003/146/literatur.pdf). The fracture toughness lies approximately at 1.2. There is a need for materials that exceed at least a part of the said values if they are processed using the press ceramics process. There have been experiments already (DE 198 52 516 A1) to make available leucitic glass-ceramics for veneer frames that particularly have advantageous thermal expansion coefficients concerning the compatibility to veneer materials. DE 198 52 516 A1 does not go into the details of the mechanical properties.

The task is to make available a material that can be pressed at <1200° C. and has very good values in terms of breaking strength and fracture toughness.

SUMMARY OF THE INVENTION

It was found that a material with one of the following compositions meets these requirements surprisingly well:

| I (percent by weight) | | II (percent by weight) | | III (percent by weight) | |
|---|---|---|---|---|---|
| ZrO2 | 17-70% | ZrO2/Al2O3 | 15-70% | Al2O3 | 15-70% |
| SiO2 | 17-59% | SiO2 | 17-59% | SiO2 | 17-59% |
| Al2O3 | 2-15% | ZrO2 | 2-15% | ZrO2 | 2-15% |
| Y2O3 | 0-6% | Y2O3 | 0-6% | Y2O3 | 0-6% |
| K2O | 3-12.5% | K2O | 3-12.5% | K2O | 3-12.5% |
| Na2O | 0.2-8.5% | Na2O | 0.2-8.5% | Na2O | 0.2-8.5% |
| Li2O | 0-1.5% | Li2O | 0-1.5% | Li2O | 0-1.5% |
| CaO | 0.3-2% | CaO | 0.3-2% | CaO | 0.3-2% |
| B2O3 | 0.1-5% | B2O3 | 0.1-5% | B2O3 | 0.1-5% |
| F | 0-2.5% | F | 0-2.5% | F | 0-2.5% |
| CeO2 | 0.2-2% | CeO2 | 0.2-2% | CeO2 | 0.2-2% |
| TiO2 | 0-1.5% | TiO2 | 0-1.5% | TiO2 | 0-1.5% |

The amount of $ZrO_2$ in the glass ceramic of table 1 is preferably 40-70%.

In the above alumina or zirconia are present in relatively large amounts (columns I and III). The aluminum oxide is preferably used in nanoparticulate form, for example:

Nanotek® of the company Nanophase ($Al_2O_3$, purity 99.95+ wt. %, average particle size 47 nm (determined via SSA); SSA=35 $m^2/g$ (BET); white powder; density of the powder=0.26 g/cc, true density=3.6 g/cc; morphology=spherical); or Taimicron® of the company Teimei with primary particle sizes of 0.007 to 0.2 micrometer.

DETAILED DESCRIPTION

The zirconium oxide is preferably unstabilized or partly stabilized. The materials are particularly of the type Tosoh TZO, TZ-3Y (94.8 wt. %, $ZrO_2$, 5.1 wt, % $Y_2O_3$), TZ-3YS (94.8 wt. % $ZrO_2$, 5.1 wt. % $Y_2O_3$, "smooth flowing grade"), TZ-3YS-E ($ZrO_2$ with 3 mol % $Y_2O_3$, "uniformly dispersed"), TZ5Y, TZ 5YS, TZ 5Y E (analogous with 5 mol % $Y_2O_3$).

The material in accordance with the invention is preferably pressable at 880 to 1200° C.

Naturally it is possible to add small quantities of ceramic pigments that are common in the dental technology for the characterization in terms of color without essentially damaging the mechanical properties.

Preferred materials have a linear thermal expansion coefficient of 6.8 to 14.5×$10^{-6}$ $K^{-1}$.

Preferred materials have a break strength of 250 to 420 MPa and a fracture toughness of 3.0 to 4.0.

The materials are preferably used for all-ceramic frames. They can be aesthetically adjusted to the requirements of artificial dental prosthetics by fusing the veneer materials.

The material can be compressed in standard dental press furnaces at a maximal working temperature of 1200° C. The shaping can take place as per the lost shape in standard phosphate bound investment. It is also possible to use the material in the form of presintered, cylindrical pellets.

The advantage of the material in accordance with the invention is particularly that the unrestricted use in the molar area is possible where particularly large forces take effect. Particularly, smaller bridges comprising the material in accordance with the invention can be used in these molar areas. That means an expansion of the application of press ceramics in restorative dentistry.

The following composition is an example for a glass-ceramic in accordance with the invention:

| | |
|---|---|
| ZrO$_2$ (with 3 mol Y$_2$O$_3$) | 55.0 wt. % |
| SiO$_2$ | 25.7 wt. % |
| Al$_2$O$_3$ | 4.2 wt. % |
| (Y$_2$O$_3$) | — % |
| K$_2$O | 4.7 wt. % |
| Na$_2$O | 4.4 wt. % |
| Li$_2$O | 0.5 wt. % |
| CaO | 0.4 wt. % |
| B$_2$O$_3$ | 2.5 wt. % |
| F | 1.4 wt. % |
| CeO$_2$ | 0.8 wt. % |
| TiO$_2$ | 0.5 wt. % |

The material has a breaking strength of [390±40] and a fracture toughness of [3.4].

I claim:

1. A pressable glass-ceramic composition for dental purposes comprising:

| | |
|---|---|
| ZrO$_2$ | 40-70 wt. %; |
| SiO$_2$ | 17-59 wt. %; |
| Al$_2$O$_3$ | 2-15 wt. %; |
| Y$_2$O$_3$ | 0-6 wt. %; |
| K$_2$O | 3-12.5 wt. %; |
| Na$_2$O | 0.2-8.5 wt. %; |
| Li$_2$O | 0-1.5 wt. %; |
| CaO | 0.3-2 wt. %; |
| B$_2$O$_3$ | 0.1-5 wt. %; |
| F | 0-2.5 wt. %; |
| CeO$_2$ | 0.2-2 wt. %; and |
| TiO$_2$ | 0-1.5 wt. %; | and being pressable in a dental furnace at a temperature of 880 to 1200° C.

2. Glass-ceramic composition in accordance with claim 1, further comprising additional ceramic colored pigments.

3. Glass-ceramic composition in accordance with claim 1, having a linear thermal expansion coefficient of 6.8 to 14.5× $10^{-6}$ K$^{-1}$.

4. Glass-ceramic composition in accordance with claim 1, having a breaking strength of 250 to 420 MPa.

5. Glass-ceramic composition in accordance with claim 1, having a fracture toughness of 3.0 to 4.0 MPa.

* * * * *